(12) United States Patent
Cheng

(10) Patent No.: US 8,808,396 B2
(45) Date of Patent: Aug. 19, 2014

(54) PROSTHETIC FOOT STRUCTURE

(76) Inventor: Yao-Teng Cheng, Taoyuan (TW)

(*) Notice: Subject to any disclaimer, the term of this patent is extended or adjusted under 35 U.S.C. 154(b) by 96 days.

(21) Appl. No.: 13/594,877

(22) Filed: Aug. 27, 2012

(65) Prior Publication Data

US 2014/0058530 A1    Feb. 27, 2014

(51) Int. Cl.
*A61F 2/66*    (2006.01)
*A61F 2/50*    (2006.01)

(52) U.S. Cl.
CPC ........... *A61F 2/66* (2013.01); *A61F 2002/6664* (2013.01); *A61F 2002/5083* (2013.01); *A61F 2002/5007* (2013.01)
USPC ......................................................... 623/55

(58) Field of Classification Search
CPC ................ A61F 2002/6657; A61F 2002/6664
USPC ......................................................... 623/55
See application file for complete search history.

(56) References Cited

FOREIGN PATENT DOCUMENTS

| KR | 2000-0047310 A | * | 7/2000 | ................ A61F 2/60 |
| SU | 560606 | * | 7/1975 | ................ A61F 2/66 |
| WO | WO 02/02034 A1 | * | 1/2002 | ................ A61F 2/66 |

* cited by examiner

*Primary Examiner* — David H Willse
(74) *Attorney, Agent, or Firm* — Leong C. Lei

(57) ABSTRACT

A prosthetic foot structure comprises a mounting case, a first curved flexible member, a second curved flexible member, an upper block, a lower block, and an elastic body. The first curved flexible member defines an opening. A plurality of bolts are provided for affixing the first curved flexible member to the mounting case. The second curved flexible member extends through the opening of the first curved flexible member in a direction generally opposite to the first curved flexible member. The upper block and the lower block are fastened together by a screw. The second curved flexible member is fastened to the lower block by bolts. The upper block, the lower block, and the second curved flexible member are mounted in the mounting case by a pin. The elastic body is placed against the second curved flexible member and snugly fitted in the opening of the first curved flexible member.

10 Claims, 8 Drawing Sheets

PROSTHETIC FOOT STRUCTURE

TECHNICAL FIELD OF THE INVENTION

The present invention relates to a prosthetic foot structure that can be dissembled quickly and replaced with an elastic body according to a user's condition.

DESCRIPTION OF THE PRIOR ART

A great advancement has been made in the technology of prosthetic legs. A typical prosthetic leg basically includes a custom fitted socket, a pylori, and a foot. An ideal prosthetic leg should be comfortable and easy to put on and take off, be easily adjustable, and look natural. Generally, users of prosthetic legs have different heights, weights, and habits, and they often walk in different environments. Although a conventional foot structure for prosthetic legs can provide cushion function, it cannot be adjusted according to the user's condition and the environment, so that it may cause discomfort to the user while in walking. For this reason, there is a need for further improvement.

SUMMARY OF THE INVENTION

The primary object of the present invention is to provide a prosthetic foot structure that has a proper cushion.

The secondary object of the present invention is to provide a prosthetic foot structure that can be disassembled quickly and replaced with an elastic body according to a user's condition.

According to one aspect of the present invention, the prosthetic foot structure comprises a mounting case, a first curved flexible member, a second curved flexible member, an upper block, a lower block, and an elastic body. The mounting case defines a space therein, two pin holes at two sides thereof, and a plurality of threaded holes at a back thereof. The first curved flexible member extends downwardly at a slope. The first curved flexible member defines a plurality of holes at an upper section thereof and defines an opening at a section below the upper section thereof, wherein a plurality of bolts are fitted through the holes of the first curved flexible member and into the threaded holes of said mounting case for affixing the first curved flexible member to the mounting case. The second curved flexible member extends downwardly at a slope. The second curved flexible member defines a plurality of holes at an upper section thereof. The upper block defines a through hole at an upper portion thereof and a mounting recess. The lower block has a rail portion corresponding to the mounting recess of the upper block and defines a plurality of threaded holes. The upper block and the lower block are fastened together by sliding the rail portion of the lower block into the mounting recess of the upper block and using a screw fitted through one of the holes of the second curved flexible member and one of the threaded holes of the lower block to engage with the upper block. The second curved flexible member is fastened to the lower block by using bolts fitted through the other holes of the second curved flexible member and into the other threaded holes of the lower block. The upper block, the lower block, and the upper section of the second curved flexible member are mounted in the space of the mounting case by inserting a pin in the through hole of the upper block and the pin holes of the mounting case. The second curved flexible member extends downwardly through the opening of the first curved flexible member in a direction generally opposite to the first curved flexible member. The elastic body is placed against a top surface of the second curved flexible member and snugly fitted in the opening of the first curved flexible member, from a bottom surface of the first curved flexible member, to abut the upper block.

According to another aspect of the present invention, the prosthetic foot structure comprises a mounting case, a curved flexible member, and an elastic body. The mounting case defines a space therein, two pin holes at two sides thereof; and a plurality of threaded holes at a back thereof. The curved flexible member extends downwardly at a slope. The curved flexible member defines a plurality of holes at an upper section thereof and defines an opening at a section below the upper section thereof, wherein a plurality of bolts are fitted through the holes of the curved flexible member and into the threaded holes of the mounting case for affixing the curved flexible member to the mounting case. The elastic body has a protrusion defining a through hole. The elastic body extends downwardly at a slope in a direction generally opposite to the curved flexible member and is mounted to the curved flexible member, wherein the protrusion of the elastic body is snugly fitted through the opening of the curved flexible member from a bottom surface of the curved flexible member and fixed to the mounting case by inserting a pin in the pin holes of the mounting case and the through hole of the protrusion of the elastic body.

Other objects, advantages, and novel features of the present invention will become more apparent from the following detailed description when taken in conjunction with the accompanying drawings.

DETAILED DESCRIPTION OF THE PREFERRED EMBODIMENTS

Figure 1:
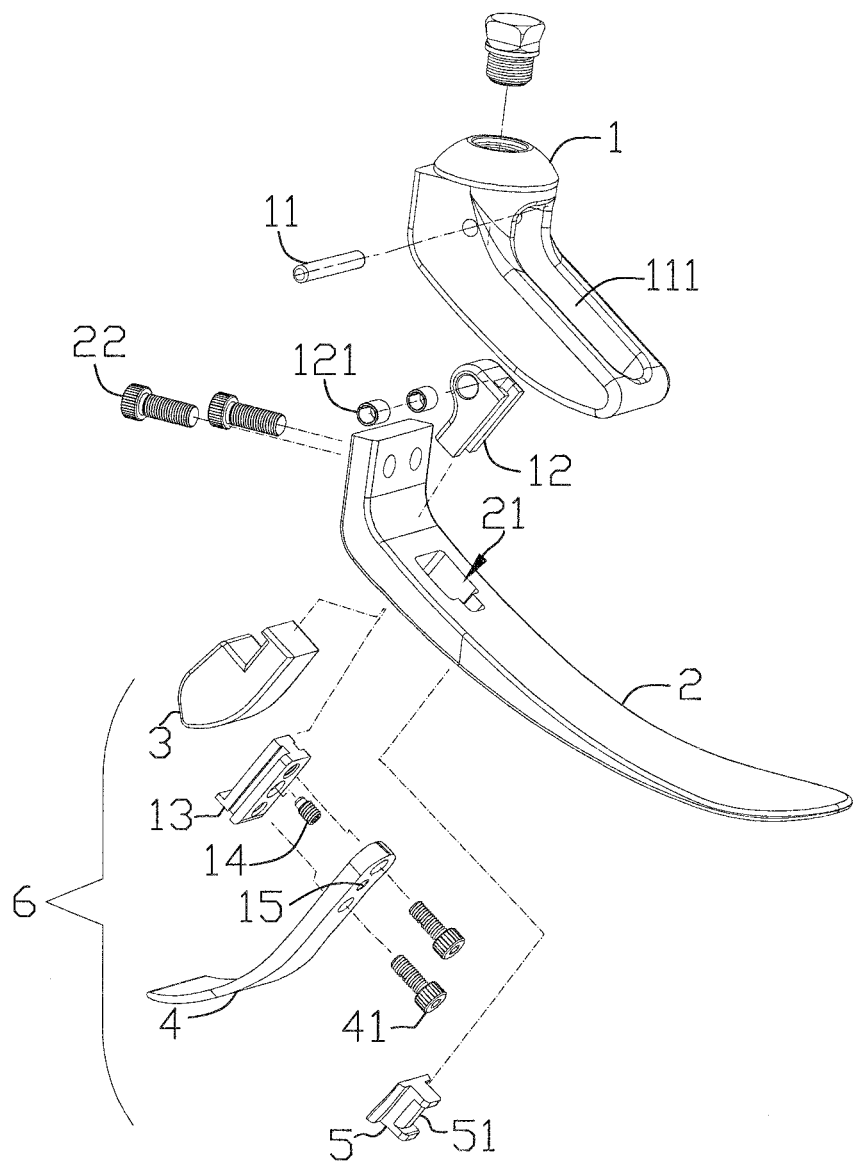
FIG. 1 shows an exploded view of a first embodiment of the present invention.
Figure 2:
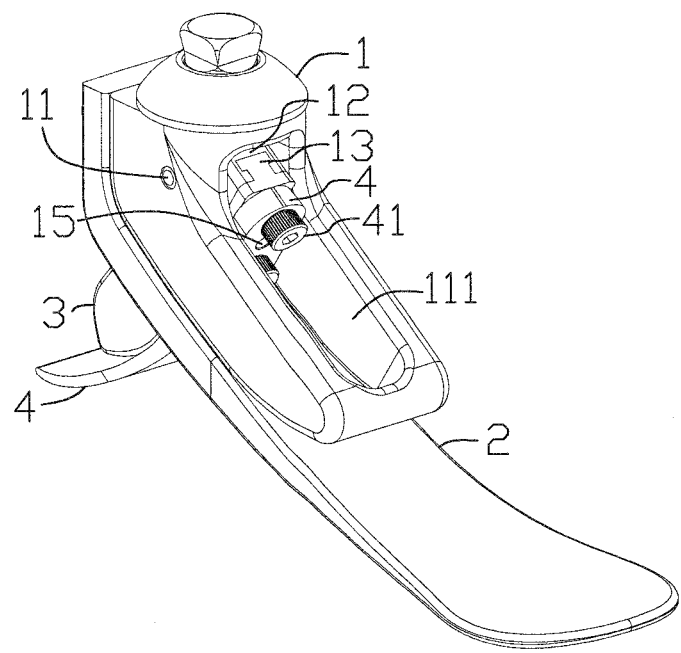
FIG. 2 shows a 3-dimensional assembled view of the first embodiment of the present invention.
Figure 3:
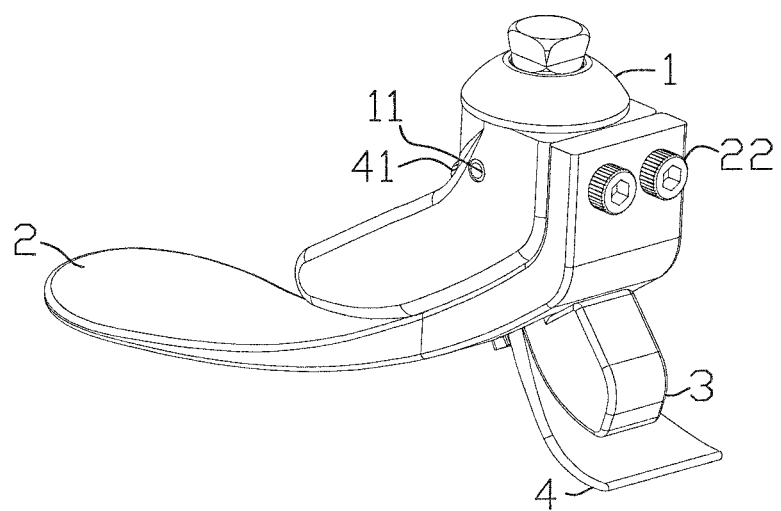
FIG. 3 shows another 3-dimensional assembled view of the first embodiment of the present invention.
Figure 4:
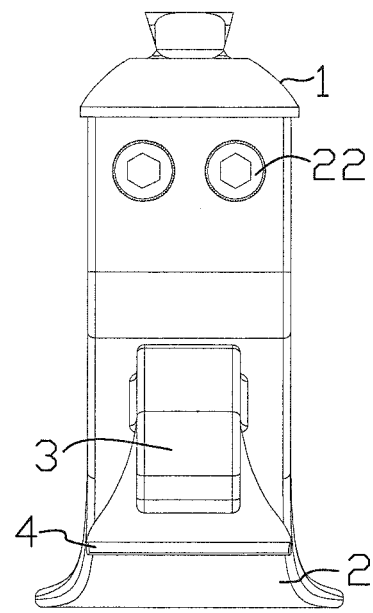
FIG. 4 shows a rear view of the first embodiment of the present invention.
Figure 5:
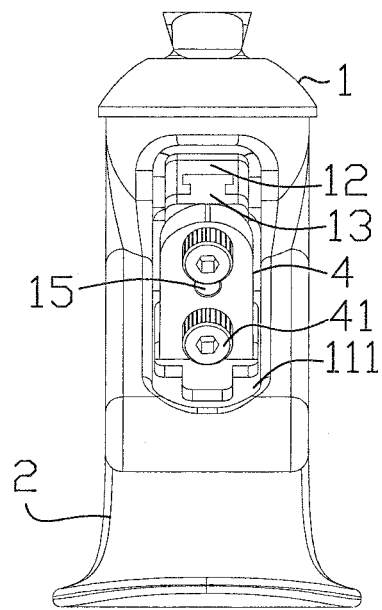
FIG. 5 shows a front view of the first embodiment of the present invention.
Figure 6:
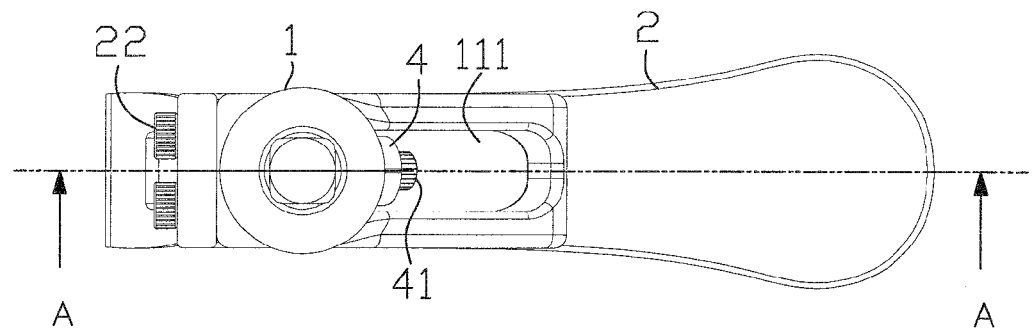
FIG. 6 shows a top view of the first embodiment of the present invention.
Figure 6A:
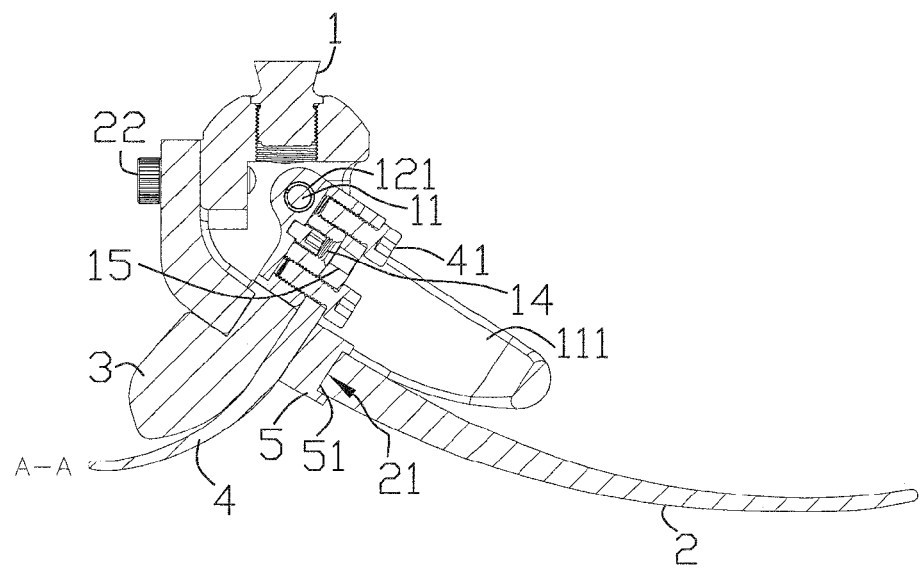
FIG. 6A shows a sectional view taken along a line A-A in FIG. 6.
Figure 7:
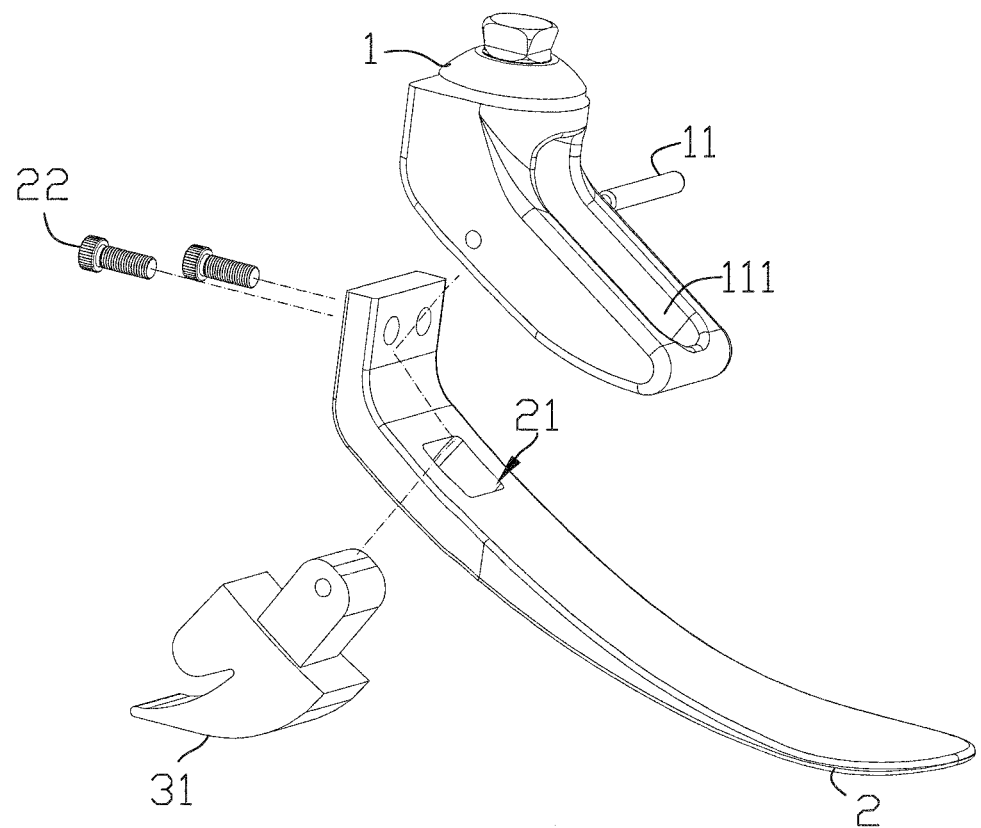
FIG. 7 shows an exploded view of a second embodiment of the present invention.
Figure 8:
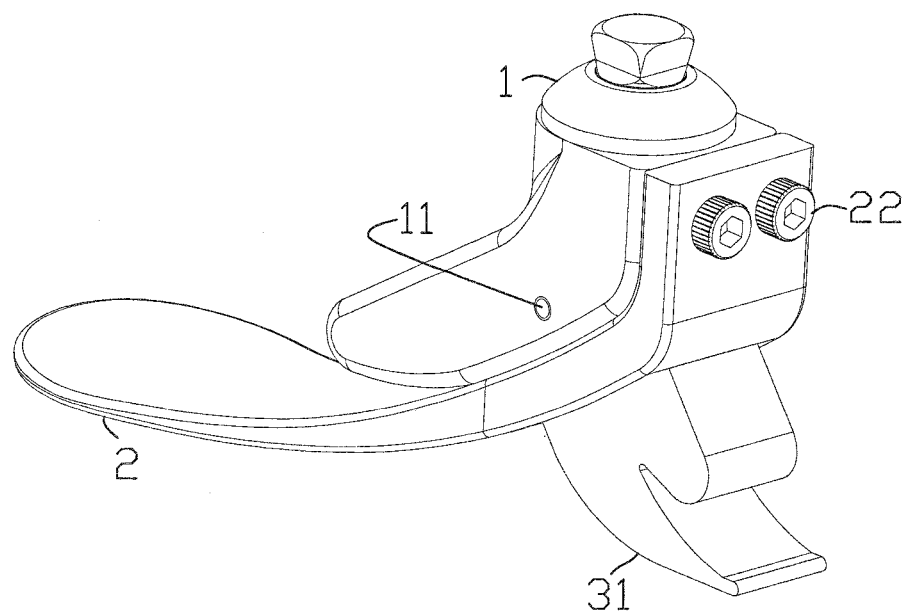
FIG. 8 shows a 3-dimensional assembled view of the second embodiment of the present invention.
Figure 9:
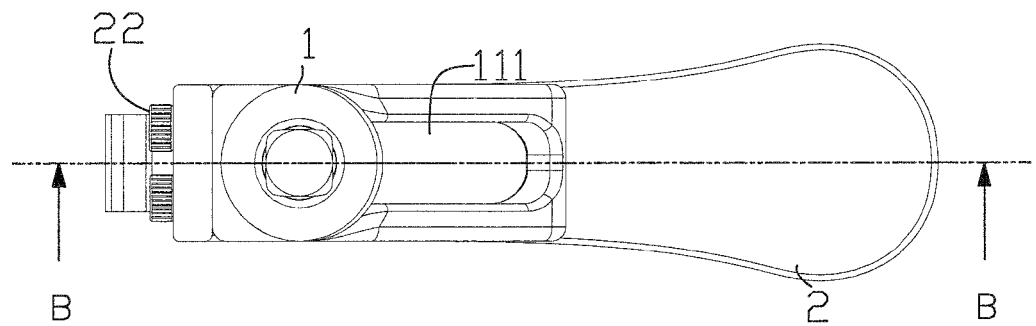
FIG. 9 shows a top view of the second embodiment of the present invention.
Figure 9A:
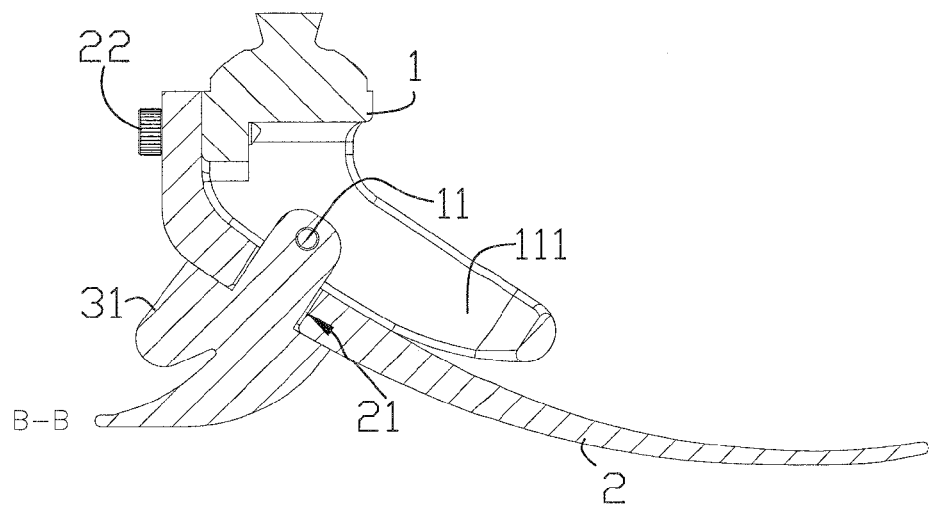
FIG. 9A shows a sectional view taken along a line B-B in FIG. 9.

Referring to FIG. 1 through 6A, a prosthetic foot structure according to a first embodiment of the present invention is shown, which generally comprises a mounting case 1, a first curved flexible member 2, and a quick-mounting assembly 6, wherein the quick-mounting assembly 6 generally includes an upper block 12, a lower block 13, a second curved flexible member 4, an elastic body 3, and an elastic mating part 5.

The mounting case 1 defines a space 111 therein, two pin holes at two sides thereof, and a plurality of threaded holes (not shown) at a back thereof; wherein the two pin holes communicates with the space 111.

The first curved flexible member 2 extends downwardly at a slope, wherein the first curved flexible member 2 defines a plurality of holes, corresponding to the threaded holes of the mounting case 1, at an upper section thereof and defines an opening 21 at a section below the upper section thereof.

A plurality of bolts 22 are fitted through the holes of the first curved flexible member 2 and into the threaded holes of the mounting case 1 for affixing the first curved flexible member 2 to the mounting case 1.

The second curved flexible member 4 extends downwardly at a slope, wherein the second curved flexible member 4 defines a plurality of holes 15 at an upper section thereof.

The upper block 12 defines a through hole at an upper portion thereof and a mounting recess. The lower block 13 has a rail portion corresponding to the mounting recess of the upper block 12 and defines a plurality of threaded holes corresponding to the holes of the second curved flexible member 4. The upper block 12 and the lower block 13 are fastened together by sliding the rail portion of the lower block 13 into the mounting recess of the upper block 12 and using a screw 14 fitted through one of the holes of the second curved flexible member 4 and one of the threaded holes of the lower block 13 to engage with the upper block 12. The second curved flexible member 4 is fastened to the lower block 13 by using bolts 41 fitted through the other holes of the second curved flexible member 4 and into the other threaded holes of the lower block 13. The upper block 12, the lower block 13, and the upper section of the second curved flexible member 4 are mounted in the space 111 of the mounting case 1 by inserting a pin 11 in the through hole of the upper block 12 and the two pin holes of the mounting case 1. Preferably, two bushes 121 are placed in the through hole of the upper block 12 and fitted around the pin 11. Furthermore, the second curved flexible member 4 extends downwardly through the opening 21 of the first curved flexible member 2 in a direction generally opposite to the first curved flexible member 2.

The elastic body 3 is placed against a top surface of the second curved flexible member 4 and snugly fitted in the opening 21 of the first curved flexible member 2, from a bottom surface of the first curved flexible member 2, to abut the first block 12. The elastic mating member 5 can facilitate the elastic body 3 to be snugly fitted in the opening 21 of the first curved flexible member 2. Furthermore, the elastic body 3 has a curved surface conforming to the top surface of the second curved flexible member 4 and defines a first engagement recess at a surface opposite to the curved surface. The elastic mating part 5, which defines a second engagement recess 51, is placed against a bottom surface of the second curved flexible member 4. The first curved flexible member 2 can engage with the first engagement recess of the elastic body 3 and the second engagement recess 51 of the elastic mating part 5 at its opening 21. The use of the elastic body 3 can protect the second curved flexible member 4 and prolong the service life of the second curved flexible member 4.

The first curved flexible member 2 and the second curved flexible member 4 can be made of high polymer material, which can undergo elastic deformation. The high polymer can be selected from the group consisting of synthetic rubber, EPDM rubber, natural rubber, styrene-butadiene rubber, thermoplastic elastomer, thermoplastic polyurethane, fiberglass, carbon fiber, and engineering plastics. Thus, they are not broken easily.

The elastic body 3 and the elastic mating part 5 can be made of high polymer material, which can undergo elastic deformation and has a good shock absorption. Thus, they can further absorb shock energy and increase the capability of the elastic deformation, thereby making the foot structure be with proper cushion.

Furthermore, the mounting case 1 can be made of metal or high polymer material. The metal can be selected from the group consisting of aluminum alloy and titanium alloy. The high polymer material can be selected from the group consisting of synthetic rubber, EPDM rubber, natural rubber, styrene-butadiene rubber, thermoplastic elastomer, and thermoplastic polyurethane.

For replacing the elastic body 3, a technician can unscrew the screw 14 by using a screwdriver, so that the lower block 13 together with the second curved flexible member 4 can be taken out of the mounting case 1, and then the original plastic body 3 can be replaced with a new or another plastic body, according to a user's condition or habit, to allow the user feel comfortable while in walking.

Referring to FIGS. 7 through 9A, a second embodiment of the present invention is shown, which generally comprises a mounting case 1, a curved flexible member 2, and an elastic body 31.

The mounting case 1 defines a space 111 therein, two pin holes at two sides thereof, and a plurality of threaded holes (not shown) at a back thereof; wherein the two pin holes communicates with the space 111.

The curved flexible member 2 extends downwardly at a slope, wherein the curved flexible member 2 defines a plurality of holes, corresponding to the threaded holes of the mounting case 1, at an upper section thereof and defines an opening 21 at a section below the upper section thereof.

A plurality of bolts 22 are fitted through the holes of the curved flexible member 2 and into the threaded holes of the mounting case 1 for affixing the curved flexible member 2 to the mounting case 1.

The elastic body 31 has a protrusion defining a through hole. The elastic body 31, which extends downwardly at a slope in a direction generally opposite to the curved flexible member 2, is mounted to the curved flexible member 2. The protrusion of the elastic body 31 is snugly fitted through the opening 21 of the curved flexible member 2 from a bottom surface of the curved flexible member 2 and fixed to the mounting case 1 by inserting a pin 11 in the pin holes of the mounting case 1 and the through hole of the protrusion of the elastic body 31.

The materials for manufacturing the mounting case 1, the curved flexible member 2, and the elastic body 31 are basically the same as the corresponding components of the first embodiment. Thus, a detailed description therefor is eliminated here.

As shown, the second embodiment employs fewer components than the first embodiment to accomplish a prosthetic foot structure that can be rapidly disassembled and replaced with another elastic body according to a user's condition, to allow the user to feel comfortable while in walking.

Figure 10:
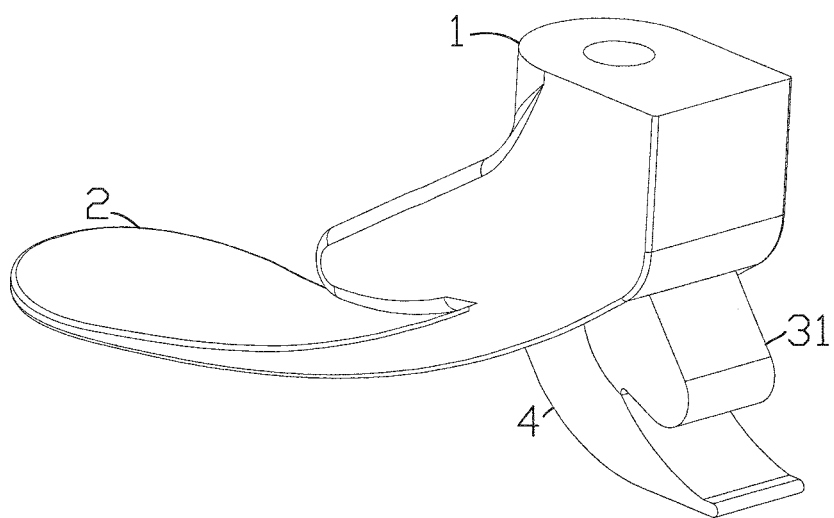
FIG. 10 shows another preferred embodiment of the present invention.
Figure 10A:
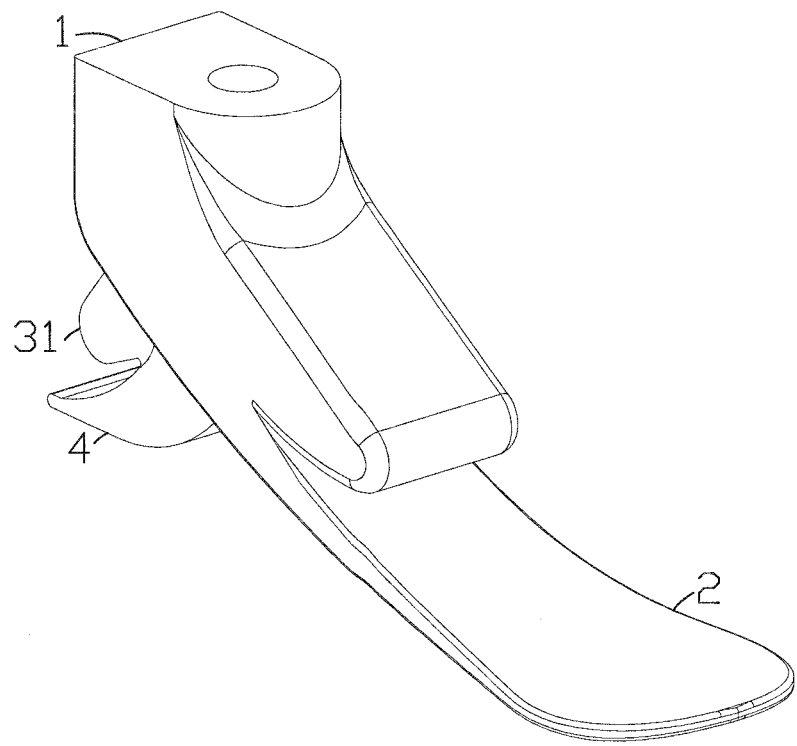
FIG. 10A shows another perspective view of the preferred embodiment shown in FIG. 10.

FIGS. 10 and 10A illustrate another preferred embodiment of the present invention.

Although the present invention has been described with a certain degree of particularity, it is understood that the present disclosure is made by way of example only and the combination and arrangement of parts may be resorted to without departing from the spirit and scope of the invention hereinafter claimed.

I claim:

1. A prosthetic foot structure, comprising: a mounting case, which has a lower portion forming an extension, the extension having two sides in which pin holes are formed and which define therebetween a space; a quick-mounting assembly, which comprises an upper block and a lower block, the quick-mounting assembly being received in the space and mounted to the extension of the mounting case; a first curved flexible member, which forms an opening in the middle thereof; a second curved flexible member, which defines a plurality of holes in an upper section thereof corresponding to threaded holes defined in a front side of the lower block, bolts being received in the threaded holes; an elastic body, which is arranged between the first curved flexible member and the second curved flexible member to provide a function of cushioning and shock absorption;

characterized in that the upper block corresponds to the first curved flexible member and the lower block corresponds to the second curved flexible member or the mounting case, fastening being realized with screwing, tenon, or pin for coupling.

2. The prosthetic foot structure according to claim 1, wherein the elastic body is embedded in corresponding positions in the mounting case and the first curved flexible member for coupling with features of projection and recess.

3. The prosthetic foot structure according to claim 1, wherein the first curved flexible member and the second curved flexible member are made of polymer selected from synthetic rubber, ethylene propylene diene monomer (EPDM) rubber, natural rubber (NR), styrene-butadiene rubber (SBR), thermoplastic elastomer (TPE), thermoplastic polyurethane (TPU), fiber glass, carbon fiber, and engineering plastics.

4. The prosthetic foot structure according to claim 1, wherein the mounting case is made of a metallic material selected from aluminum alloy and titanium alloy.

5. The prosthetic foot structure according to claim 1, wherein the mounting case is made of polymer selected from synthetic rubber, ethylene propylene diene monomer (EPDM) rubber, natural rubber (NR), styrene-butadiene rubber (SBR), thermoplastic elastomer (TPE), thermoplastic polyurethane (TPU).

6. A prosthetic foot structure, comprising: a mounting case, which has a lower portion forming an extension, the extension having two sides in which pin holes are formed and which define therebetween a space; a first curved flexible member, which forms an opening in the middle thereof and defines a plurality of holes in an upper section thereof corresponding to threaded holes formed in a rear side of the mounting case, bolts being received in the threaded hole; a second curved flexible member, which defines a plurality of holes in an upper section thereof corresponding to threaded holes defined in a front side of a lower block; a quick-mounting assembly, which comprises an upper block and the lower block, the quick-mounting assembly being received in the space and mounted to the extension of the mounting case; an elastic body, which is arranged below the first curved flexible member to provide a function of cushioning and shock absorption.

7. The prosthetic foot structure according to claim 6, wherein the elastic body provides a function of cushioning, fastening being realized with bearing, or pin for coupling.

8. The prosthetic foot structure according to claim 6, wherein the first curved flexible member and the second curved flexible member are made of polymer selected from synthetic rubber, ethylene propylene diene monomer (EPDM) rubber, natural rubber (NR), styrene-butadiene rubber (SBR), thermoplastic elastomer (TPE), thermoplastic polyurethane (TPU), fiber glass, carbon fiber, and engineering plastics.

9. The prosthetic foot structure according to claim 6, wherein the mounting case is made of a metallic material selected from aluminum alloy and titanium alloy.

10. The prosthetic foot structure according to claim 6, wherein the mounting case is made of polymer selected from synthetic rubber, ethylene propylene diene monomer (EPDM) rubber, natural rubber (NR), styrene-butadiene rubber (SBR), thermoplastic elastomer (TPE), thermoplastic polyurethane (TPU).

* * * * *